(12) United States Patent
Manfredi et al.

(10) Patent No.: US 9,855,226 B2
(45) Date of Patent: Jan. 2, 2018

(54) D-METHADONE FOR THE TREATMENT OF PSYCHIATRIC SYMPTOMS

(71) Applicant: Relmada Therapeutics, Inc., New York, NY (US)

(72) Inventors: Paolo L. Manfredi, New York, NY (US); Charles E. Inturrisi, New York, NY (US)

(73) Assignee: Relmada Therapeutics, Inc., New York, NY (US)

( * ) Notice: Subject to any disclaimer, the term of this patent is extended or adjusted under 35 U.S.C. 154(b) by 0 days.

(21) Appl. No.: 15/204,052

(22) Filed: Jul. 7, 2016

(65) Prior Publication Data
US 2016/0310450 A1 Oct. 27, 2016

Related U.S. Application Data

(63) Continuation of application No. 13/803,375, filed on Mar. 14, 2013, now Pat. No. 9,468,611.

(60) Provisional application No. 61/706,178, filed on Sep. 27, 2012.

(51) Int. Cl.
| | |
|---|---|
| *A61K 31/137* | (2006.01) |
| *A61K 45/06* | (2006.01) |
| *A61K 9/19* | (2006.01) |
| *A61K 9/00* | (2006.01) |

(52) U.S. Cl.
CPC .......... *A61K 31/137* (2013.01); *A61K 9/0019* (2013.01); *A61K 45/06* (2013.01)

(58) Field of Classification Search
CPC ... A61K 31/137; A61K 2300/00; A61K 45/06
See application file for complete search history.

(56) References Cited

U.S. PATENT DOCUMENTS

| 6,008,258 A | 12/1999 | Inturrisi |
| 2006/0167032 A1 | 7/2006 | Galer et al. |

OTHER PUBLICATIONS

Berman, R.M. et al., "Antidepressant Effects of Ketamine in Depressed Patients," Biol. Psych. 2000;47:351-354.
Bisaga, A. et al., "Therapeutic potential of NMDA receptor antagonists in the treatment of alcohol and substance use disorders," Exp Opin Invest Drugs 2009;9(10):2233-2248.
Boyer, P.A. et al., "Chronic Administration of Imipramine and Citalopram Alters the Expression of NMDA Receptor Subunit mRNAs in Mouse Brain: A Quantitative In Situ Hybridization Study," J Mol Neurosci 1998;10:219-233.
Codd, E.E. et al., "Serotonin and Norepinephrine Uptake Inhibiting Activity of Centrally Acting Analgesics: Structural Determinants and Role in Antinociception," JPET 1995; 274(3):1263-1270.
Davis, A.M. et al., "d-Methadone Blocks Morphine Tolerance and N-Methyl-D-Aspartate-Induced Hyperalgesia," J Pharma and Exper Therap, 1999;289:1048-1053.
Elkader, A.K. et al., "Major Depressive Disorder and Patient Satisfaction in Relation to Methadone Pharmacokinetics and Pharmacodynamics in Stabilized Methadone Maintenance Patients," Journal of Clinical Psychopharmacology 2009;29(1):77-81.
Gorman, A.L. et al., The d- and l- isomers of methadone bind to the non-competitive site on the N-methyl-D-aspartate (NMDA) receptor in rat forebrain and spinal cord, Nerurosc iLett, 1997;223:5-8.
International Search Report and Written Opinion in PCT/US2013/061639, dated Nov. 26, 2013, 12 pgs.
Inturrisi, C.E., "Opioid Analgesic Therapy in Cancer Pain," Advances in Pain Research and Therapy (Foley, K.M. et al., Eds.) 1990;16:133-154.
Inturrisi, C.E., "Pharmacology of methadone and its isomers," Minerva Anestesiologica 2005;71:435-437.
Krystal, J.H. et al., "NMDA Agonists and Antagonists as Probes of Glutamatergic Dysfunction and Pharmacotherapies in Neuropsychiatric Disorders," Harv Rev Psych 1999;7(3):125-143.
Manfredi, P.L. et al., "Intravenous methadone for cancer pain unrelieved by morphine and hydromorphone: clinical observations," Pain 1997;70:99-101.
Manfredi, P.L. et al., "Methadone Analgesia in Cancer Pain Patients on Chronic Methadone Maintenance Therapy," J Pain Sympt Manag 2001;21(2):169-174.
Mitchell, T.B. et al., "Subjective and physiological responses among racemic-methadone maintenace patients in relation to relative (S)- vs. (R)-methadone exposure," Br J Clin Pharmacol 2004;58(6):609-617.
Moryl, N. et al., "Pitfalls of opioid rotation: substituting another opioid for methadone in patients with cancer pain," Pain 2002;96(3):325-328.
Office Action in U.S. Appl. No. 13/803,375, dated Apr. 9, 2015, 16 pgs.
Office Action in U.S. Appl. No. 13/803,375, dated Feb. 11, 2016, 12 pgs.
Office Action in U.S. Appl. No. 13/803,375, dated Jun. 2, 2016, 6 pgs.
Sanacora, G. et al., "Subtype-Specific Alterations of γ-Aminobutyric Acid and Glutamate in Patients with Major Depression," Arch Gen Psychiatry 2004;61:705-713.
Shimoyama, N. et al., "d-Methadone Is Antinociceptive in the Rat Formalin Test," J Pharma and Exper Therap 1997;283:648-652.
Skolnick, P. et al., "Adaptation of N-Methyl-D-Aspartate (NMDA) Receptors following Antidepressant Treatment: Implications for the Pharmacotherapy of Depression," Pharmacopsychiatry 1996;29(1):23-26.

(Continued)

*Primary Examiner* — Sreeni Padmanabhan
*Assistant Examiner* — Jody Karol
(74) *Attorney, Agent, or Firm* — Wood Herron & Evans LLP

(57) ABSTRACT

The present invention relates to a method of treating psychiatric symptoms in a subject having a NMDA receptor and a NE receptor which includes administering d-methadone, d-methadol, d-alpha-acetylmethadol, l-alpha-acetylmethadol, d-alpha-normethadol, l-alpha-normethadol, pharmaceutically acceptable salts thereof, or mixtures thereof, to the subject under conditions effective for the substance to bind to the NMDA receptor and NE receptor of the subject.

20 Claims, 1 Drawing Sheet

(56) References Cited

OTHER PUBLICATIONS

Snyder, F.R. "Methadone and Acetylmethadol: Systematic Versus Differential Effects on Affective States," Pharmacology Biochemistry and Behavior 1986;25(1):310 (Abstract).

Tennant, F.S. Jr., "(−)-a-Acetylmethadol for Treatment of Chronic Pain Patients Who Abuse Opioids," Drug and Alcohol Dependence 1983;12:243-247.

Trullas, R. et al., "Functional antagonists at the NMDA receptor complex exhibit antidepressant actions," Eur J Pharmacol 1990;185:1-10.

Yilmaz, A. et al., "Prolonged effect of an anesthetic dose of ketamine on behavioral despair," Pharmacol Biochem Behav 2002;71:341-344.

Zarate, C.A., Jr. et al., "A Randomized Trial of an N-methyl-D-aspartate Antagonist in Treatment-Resistant Major Depression," Arch Gen Psy 2006;63:856-864.

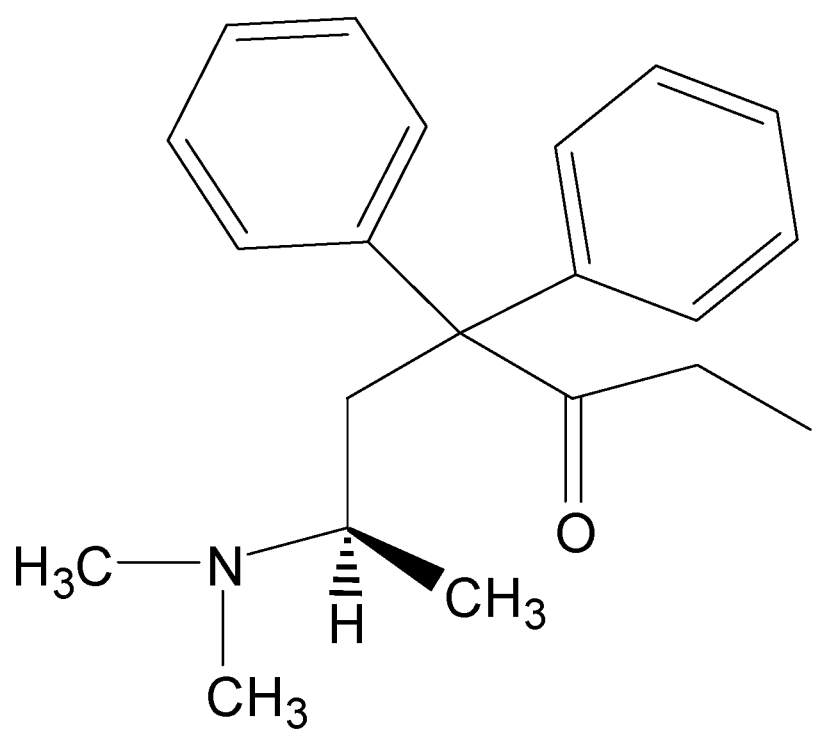
d-Methadone

D-METHADONE FOR THE TREATMENT OF PSYCHIATRIC SYMPTOMS

CROSS-REFERENCE TO RELATED APPLICATIONS

This application is a continuation of U.S. patent application Ser. No. 13/803,375, entitled "d-methadone for the Treatment of Psychiatric Symptoms," filed on Mar. 14, 2013, which claims the benefit of the filing date of U.S. Patent Application Ser. No. 61/706,178, entitled "d-methadone for the Treatment of Psychiatric Symptoms," filed on Sep. 27, 2012, the disclosures of which are incorporated by reference herein in their entireties.

FIELD OF THE INVENTION

The present invention relates to the treatment of psychiatric conditions, and to compounds for the treatment of psychiatric conditions.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Many psychological and psychiatric conditions (some of which can be severe and debilitating) affect individuals. These conditions include depression, anxiety disorders, and fatigue. Depression is a mental disorder characterized by episodes of all-encompassing low mood accompanied by low self-esteem and loss of interest or pleasure in normally enjoyable activities. The term "depression" may denote this syndrome, but may refer to other mood disorders or to lower mood states lacking clinical significance. Major depressive disorder is a clinically-diagnosed and disabling condition that adversely affects a person's family, work, and/or school life, sleeping and eating habits, general health, and can lead to self-harm.

Presently, individuals suffering from depression are often treated with antidepressant medication. The treatment of depression was revolutionized in the 1950s by the discovery of monoamine oxidase inhibitors (MAOIs) and tricyclic antidepressants (TCAs). This was followed in the 1980s by the advent of the first selective serotonin reuptake inhibitor (SSRI).

Many antidepressant medications work via mechanisms that ultimately increase the amount and availability of neurotransmitters for signaling between nerve cells. In the brain, messages are passed between two nerve cells via a chemical synapse, a small gap between the cells. The presynaptic cell releases neurotransmitters (e.g., serotonin, norepinephrine, etc.) into the synapse. The neurotransmitters are then recognized by receptors on the surface of the postsynaptic cell (i.e., the recipient cell). Following the completion of this process, the large majority of the neurotransmitters are released from the receptors and taken up by monoamine transporters into the presynaptic cell (a process called reuptake). MAOIs, TCAs, and SSRIs function by influencing this process.

As is known to those of ordinary skill in the art, MAOIs are chemicals which inhibit the activity of the monoamine oxidase enzyme family, thus preventing the breakdown of monoamine neurotransmitters and increasing their availability. In the past, MAOIs were prescribed for those resistant to tricyclic antidepressant therapy. However, because of potentially problematic dietary and drug interactions, MAOIs have historically been used only when other classes of antidepressant drugs (e.g., selective serotonin reuptake inhibitors and tricyclic antidepressants) have failed.

Tricyclic antidepressants (TCAs) are heterocyclic chemical compounds, the majority of which act primarily as serotonin-norepinephrine reuptake inhibitors (SNRIs) by blocking the serotonin transporter and the norepinephrine (NE) transporter, respectively. This results in an elevation of the synaptic concentrations of these neurotransmitters, and therefore an enhancement of neurotransmission.

In recent times, TCAs have been largely replaced in clinical use by newer antidepressants such as the selective serotonin reuptake inhibitors (SSRIs), which typically have more favorable side-effects profiles.

Selective serotonin re-uptake inhibitors (SSRIs)—such as Prozac®, Zoloft®, and Paxil®—are a class of compounds that increase the extracellular level of the neurotransmitter serotonin by inhibiting its reuptake into the presynaptic cell, increasing the level of serotonin in the synaptic cleft available to bind to the postsynaptic receptor. As a result, the serotonin stays in the synaptic gap longer than it normally would, and may repeatedly stimulate the receptors of the recipient cell.

Apart from MAOIs, TCAs, and SSRIs, additional antidepressant medications have been developed. However, since the advent of SSRIs in the 1980s, newer medications are largely "me too" drugs that exert their primary biochemical effects by increasing the intra-synaptic levels of monoamines.

Typically medications such as MAOIs, TCAs, and SSRIs take weeks to achieve their full effects. For example, high serotonin levels (due to the effects of some antidepressant medications, such as SSRIs) will not only activate the postsynaptic receptors, but also presynaptic autoreceptors, which serve as a feedback sensor for the cell. Activation of the autoreceptors (by agonists like serotonin) triggers a reduction of serotonin production. The resulting serotonin deficiency persists for some time, although the body gradually adapts to this situation by lowering the sensitivity of the autoreceptors.

These slow neurophysiological adaptations of the brain tissue are the reason why several weeks of continuous SSRI use is generally necessary for the antidepressant effect to become fully manifested, and why increased anxiety is a common side effect in the first few days or weeks of use.

Unfortunately, during this lag time, patients continue to suffer from symptoms of depression. Indeed, this lag period in onset of action of traditional antidepressants (of up to several weeks) results in risk of self-harm as well as harm to the patients' personal and professional lives, especially in the first days after starting antidepressant treatment. Furthermore not all patients respond to drugs that increase the intra-synaptic levels of monoamines (such as serotonin).

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

As described above, current medications for depression suffer several drawbacks (e.g., taking long periods of time to achieve their full effects). Furthermore, available antidepressants are ineffective in a relatively high percentage of depressed patients. Furthermore, several psychiatric symptoms, in addition to depression, such as anxiety disorders, fatigue, psychological symptoms associated with withdrawal from various substances, are inadequately treated by the available psychiatric drugs, including anxiolytics, neuroleptics, antidepressants, mood stabilizers. And, although medications have been developed and used to treat conditions such as depression, not all patients respond to drugs that increase the intra-synaptic levels of monoamines.

In view of the drawbacks listed above, pharmacological strategies that (1) have rapid onset of antidepressant effects (within hours or even a few days), (2) are sustained, would have an enormous impact on public health, and (3) are effective in patients refractory to available treatments.

Various aspects of the present invention are based on the discovery by the present inventors that such patients may respond to NMDA receptor antagonists (substances that bind the N-methyl-D-aspartate receptor), or a drug like d-methadone, which combines NMDA receptor antagonisms with inhibition of NE re-uptake, alone or in combination with standard therapy. Previously, those of ordinary skill in the art have not considered NMDA receptor antagonists such as d-methadone to be candidate compounds for treatment of psychiatric conditions for many reasons, including (but not limited to) the connotation of methadone (and thus d-methadone) as an addictive opioid drug. Furthermore, the lack of understanding about of the NMDA activity of d-methadone combined with its lack of substantial opioid activity, as shown by Inturrisi [See Gorman, A. L., Elliott, K. J. and Inturrisi, C. E., The d- and l-isomers of methadone bind to the non-competitive sit on the N-methyl-D-aspartate (NMDA) receptor in rat forebrain and spinal cord, NerurosciLett, 223 (1997) 5-8; Shimoyama, N. et. al, "d-methadone Is Antinociceptive in the Rat Formalin Test," J Pharma and ExperTherap, 293 (1997) pp. 648-652; Davis, A. M. and Inturrisi, C. E., "d-methadone Blocks Morphine Tolerance and N-Methyl-D-Aspartate-Induced Hyperalgesia," J Pharma and ExperTherap, 289 (1999) pp. 1048-1053. incorporated by reference herein in its entirety]. Further, even though medications such as antidepressants are still an area of major medical need, Forbes noted in May, 2102 that companies like Novartis, GSK, and AstraZeneca had ceased their neuroscience research efforts and other large pharmaceutical companies such as Merck, Pfizer and Sanofi had drastically scaled back their research, due to reasons including high placebo success rates. (See LaMattina, John, "Will Lundbeck's New Antidepressant Be a Major New Drug?" Forbes online, Pharma & Healthcare, May 22, 2012.)

Thus, one aspect of the present invention provides a method of treating psychological and psychiatric symptoms in a subject having a NMDA receptor. The method includes administering a NMDA receptor antagonist substance (such as d-methadone, d-methadol, d-alpha-acetylmethadol, l-alpha-acetylmethadol, d-alpha-normethadol, l-alpha-normethadol, pharmaceutically acceptable salts thereof, or mixtures thereof) to a subject under conditions effective for the substance to bind to the NMDA receptor of the subject and thereby relieve the subject from psychological symptoms such as depression, anxiety, fatigue, mood instability including pseudo-bulbar affect. The substance may be isolated from its enantiomer or synthetized de novo.

A second aspect of the present invention provides a method of treating psychological and psychiatric symptoms in a subject having a NE receptor. The method includes administering a substance (such as d-methadone, d-methadol, d-alpha-acetylmethadol, l-alpha-acetylmethadol, d-alpha-normethadol, l-alpha-normethadol, pharmaceutically acceptable salts thereof, or mixtures thereof) to a subject under conditions effective for the substance to bind to the NE receptor of the subject and thereby relieve the subject from psychological symptoms such as depression, anxiety, fatigue, mood instability including pseudo-bulbar affect. The substance may be isolated from its enantiomer or synthetized de novo.

Thus, various aspects of the present invention include the use of d-methadone for the treatment of depression. They also include the use of d-methadone for the acute/rapid treatment of depression. d-methadone may be used alone for the acute and chronic treatment of depression, or in combination with other antidepressants and or other NMDA antagonists.

Another aspect of the present invention includes the use of d-methadone for the treatment of anxiety, fatigue, or mood instability (including pseudobulbar affect).

Another aspect of the present invention includes the use of d-methadone for the treatment of psychological symptoms (depression, mood instability, pseudobulbar affect, dysphoria, anxiety, fatigue and others) associated with chronic pain, including cancer pain.

Another aspect of the present invention includes the use of d-methadone for the treatment of psychological symptoms (depression, mood instability, pseudobulbar affect, dysphoria, anxiety, fatigue and others) associated with cancer.

Another aspect of the present invention includes the use of d-methadone for the treatment of psychological symptoms (depression, mood instability, pseudobulbar affect, dysphoria, anxiety, fatigue and others) associated with opioid therapy.

Another aspect of the present invention includes the use of d-methadone for the treatment of psychological symptoms (including depression, mood instability, pseudobulbar affect, dysphoria, anxiety, fatigue and others) associated with withdrawal from various substances, including alcohol, tobacco, opioids, antidepressants, benzodiazepines, alone or in combination with nicotine or with antidepressants, anxiolytics, antipsychotics, mood stabilizers, lithium, stimulants, NMDA antagonists, and/or analgesics.

d-methadone may be clinically useful for some or all of the above indications alone or in combination with antidepressants, anxiolytics, antipsychotics, mood stabilizers, lithium, stimulants, NMDA antagonists, and analgesics.

Another aspect of the present invention includes the use of d-methadone orally or intravenously, for the acute treatment of depression in patients at the start of antidepressant therapy for a more rapid therapeutic onset: available antidepressants require several weeks for the onset of effects while d-methadone may be effective more rapidly, therefore avoiding or reducing the increased risk of suicide seen in patients during the first few weeks of treatment with the available antidepressants.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

The FIGURE shows the structure of d-methadone.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, current medications suffer several drawbacks (such as taking long periods of time to achieve their full effects). Furthermore, available antidepressants are ineffective in a relatively high percentage of depressed patients. Furthermore, several psychiatric symptoms, in addition to depression, such as anxiety disorders, fatigue, psychological symptoms associated with withdrawal from various substances, are inadequately treated by the available psychiatric drugs, including anxiolytics, neuroleptics, antidepressants, mood stabilizers. And, although medications have been developed and used to treat depression, not all patients respond to drugs that increase the intra-synaptic levels of monoamines.

However, the present inventors have discovered that such patients may instead respond to NMDA antagonists, or a drug like d-methadone, which combines NMDA antagonisms with inhibition of NE re-uptake, alone or in combination with standard therapy.

Thus, one aspect of the present invention provides a method of treating psychological and psychiatric symptoms in a subject having a NMDA receptor. The method includes administering a NMDA-receptor antagonist substance (such as d-methadone, d-methadol, d-alpha-acetylmethadol, l-alpha-acetylmethadol, d-alpha-normethadol, l-alpha-normethadol, pharmaceutically acceptable salts thereof, or mixtures thereof) to a subject under conditions effective for the substance to bind to the NMDA receptor of the subject and thereby relieve the subject from psychological symptoms such as depression, anxiety, fatigue, mood instability including pseudo-bulbar affect. The substance may be isolated from its enantiomer or synthetized de novo.

As described above, NMDA receptor antagonists are a class of anesthetics that antagonize, or inhibit the action of, the NMDA receptor. The NMDA receptor, a glutamate receptor, is the predominant molecular device for controlling synaptic plasticity and memory function and allows for the transfer of electrical signals between neurons in the brain and in the spinal column. For electrical signals to pass, the NMDA receptor must be open. To remain open (activated), glutamate and glycine must bind to the NMDA receptor.

Chemicals that deactivate the NMDA receptor are called antagonists. NMDA receptor antagonists fall into four categories: (1) competitive antagonists, which bind to and block the binding site of the neurotransmitter glutamate; (2) glycine antagonists, which bind to and block the glycine site; (3) noncompetitive antagonists, which inhibit NMDA receptors by binding to allosteric sites; and (4) uncompetitive antagonists, which block the ion channel by binding to a site within it. Several synthetic opioids function as NMDA receptor-antagonists, such as methadone, meperidine, dextropropoxyphene, tramadol, levorphanol, and ketobemidone.

Furthermore, (1) NMDA receptors are adaptively altered in circumscribed central nervous system (CNS) areas following chronic antidepressant (AD) therapy, and (2) behavioral studies show AD-like actions of several functional NMDA antagonists. Neurochemical studies have shown that chronic administration of NMDA antagonists to rodents leads to a down regulation of cortical β-adrenoceptors. Chronic administration of ADs to mice produces adaptive changes in radioligand binding to NMDA receptors. Studies with imipramine, electroconvulsive shock (ECS), and citalopram show that these changes develop slowly and persist for some time after treatment cessation. Changes due to these drugs are dose dependent and restricted to the cerebral cortex. [For the above, see Skolnick, P.; Layer, R. T.; Popik, P.; Nowak, G.; et al Adaptation of N-methyl-D-aspartate (NMDA) receptors following antidepressant treatment: Implications for the pharmacotherapy of depression. Pharmacopsychiatry, Vol 29(1), January 1996, 23-26, incorporated by reference herein in its entirety.] Further, radioligand-binding to the NMDA receptor is altered in frontal cortex of suicide victims. And so, the present inventors' position is that NMDA receptors may be involved in the pathophysiology of depression. Thus, the present inventors have determined that a drug like d-methadone, which combines NMDA antagonistic activity and NE re-uptake inhibition, may offer unique advantages for the treatment of psychiatric symptoms, including depression.

A second aspect of the present invention provides a method of treating psychological and psychiatric symptoms in a subject having a NE receptor. The method includes administering a substance such as d-methadone, d-methadol, d-alpha-acetylmethadol, l-alpha-acetylmethadol, d-alpha-normethadol, l-alpha-normethadol, pharmaceutically acceptable salts thereof, or mixtures thereof to a subject under conditions effective for the substance to bind to the NE receptor of the subject and thereby relieve the subject from psychological symptoms such as depression, anxiety, fatigue, mood instability including pseudo-bulbar affect. The substance may be isolated from its enantiomer or synthetized de novo.

The NE receptor is an adrenergic receptor. As is known to those of ordinary skill in the art, the adrenergic receptors (or adrenoceptors) are a class of G protein-coupled receptors that are targets of the catecholamines, especially norepinephrine and epinephrine. Many cells possess these receptors, and the binding of a catecholamine to the receptor will generally stimulate the sympathetic nervous system. Thus, various aspects of the present invention include the use of d-methadone for the treatment of depression. They also include the use of d-methadone for the acute/rapid treatment of depression. d-methadone may be used alone for the acute and chronic treatment of depression, or in combination with other antidepressants and or other NMDA antagonists.

Another aspect of the present invention includes the use of d-methadone for the treatment of psychological symptoms (depression, mood instability, pseudobulbar affect, dysphoria, anxiety, fatigue and others) associated with cancer.

Another aspect of the present invention includes the use of d-methadone for the treatment of psychological symptoms (depression, mood instability, pseudobulbar affect, dysphoria, anxiety, fatigue and others) associated with opioid therapy.

Another aspect of the present invention includes the use of d-methadone for the treatment of psychological symptoms (including depression, mood instability, pseudobulbar affect, dysphoria, anxiety, fatigue and others) associated with withdrawal from various substances, including alcohol, tobacco, opioids, antidepressants, benzodiazepines, alone or in combination with nicotine or with antidepressants, anxiolytics, antipsychotics, mood stabilizers, lithium, stimulants, NMDA antagonists, analgesics.

d-methadone may be clinically useful for some or all of the above indications alone or in combination with antidepressants, anxiolytics, antipsychotics, mood stabilizers, lithium, stimulants, NMDA antagonists, and analgesics.

Another aspect of the present invention includes the use of d-methadone orally or intravenously, for the acute treatment of depression in patients at the start of antidepressant therapy for a more rapid therapeutic onset: available antidepressants require several weeks for the onset of effects while d-methadone may be effective more rapidly, therefore avoiding or reducing the increased risk of suicide seen in patients during the first few weeks of treatment with the available antidepressants.

Another aspect of the present invention includes the use of d-methadone for the treatment of psychological symptoms at total daily dosages of 1 mg to 5000 mg.

Methadone is a synthetic opioid. It is used medically as an analgesic and a maintenance anti-addictive and reductive preparation for use by patients with opioid dependency. Because it is an acyclic analog of morphine, methadone acts on the same opioid receptors and thus has many of the same effects. Methadone is also used in managing severe chronic pain, owing to its long duration of action, extremely powerful effects, and very low cost. The term d-methadone indicates the dextrorotatory optical isomer salt of methadone, (+)-methadone HCL.

Methadone acts by binding to the μ-opioid receptor, but also has some affinity for the NMDA receptor. d-methadone is an NMDA antagonist and NE reuptake inhibitor with very weak or no opioid activity.

As described above, aspects of the present invention are directed to administering substances to a subject to affect the presence of neurotransmitters (by blocking receptors and/or reuptake of neurotransmitters). Thus, the NMDA receptor is capable of biological action, and the administering of the substance in the present invention is effective to block the biological action of the NMDA receptor. The NMDA receptor may be located in the central nervous system of the subject.

Alternatively, or additionally, the subject may have an NE receptor that is capable of biological action, and the administering of the substance in the present invention is effective to inhibit the NE reuptake at the NE receptor. The NE receptor may be located in the central nervous system of the subject.

In another embodiment of the present invention, the method may include administering more than one substance to a subject. For example, the method may further comprise administering a psychiatric drug to the subject in combination with the administering of d-methadone. In various embodiments, this psychiatric drug may be chosen from an antidepressant, an anxiolytic, a CNS stimulant, a neuroleptic, an opioid, nicotine, or another NMDA antagonist.

In various aspects and embodiments of the present invention, the administering of the psychiatric drug and the d-methadone is performed orally, nasally, rectally, transdermally, parenterally, or topically.

In various aspects and embodiments, the present invention may further comprise administering at least one d-isomer of an analog of d-methadone in combination with the administering of d-methadone.

As described above, (1) NMDA receptors are adaptively altered in circumscribed CNS areas following chronic antidepressant (AD) therapy, and (2) behavioral studies show AD-like actions of several functional NMDA antagonists. Neurochemical studies have shown that chronic administration of NMDA antagonists to rodents leads to a down regulation of cortical β-adrenoceptors. Chronic administration of ADs to mice produces adaptive changes in radioligand binding to NMDA receptors. Studies with imipramine, electroconvulsive shock (ECS), and citalopram show that these changes develop slowly and persist for some time after treatment cessation. Changes due to these drugs are dose dependent and restricted to the cerebral cortex. [See Skolnick, P.; Layer, R. T.; Popik, P.; Nowak, G.; et al Adaptation of N-methyl-D-aspartate (NMDA) receptors following antidepressant treatment: Implications for the pharmacotherapy of depression. Pharmacopsychiatry, Vol 29(1), January 1996, 23-26, incorporated by reference herein in its entirety.] Further, radioligand-binding to the NMDA receptor is altered in frontal cortex of suicide victims. Thus, NMDA receptors may be involved in the pathophysiology of depression.

NMDA receptor antagonists have anti-depressant effects in many animal models of depression, including the application of inescapable stressors, forced-swim, and tail suspension-induced immobility tests; in learned helplessness models of depression; and in animals exposed to a chronic mild stress procedure. A single dose of the NMDA antagonist ketamine hydrochloride in male Wistar rats interferes with the induction of behavioral despair for up to 10 days after its administration. Additionally, repeated administration of different classes of antidepressants—in a time frame consistent with the delayed therapeutic effects—brings about alterations in the expression of NMDA subunit messenger RNA and radioligand binding to these receptors in regions of the brain implicated in the pathophysiology of depression. (See Trullas R, Skolnick P. Functional antagonists at the NMDA receptor complex exhibit antidepressant actions. Eur J Pharmacol. 1990; 185:1-10; Yilmaz A, Schulz D, Aksoy A, Canbeyli R. Prolonged effect of an anesthetic dose of ketamine on behavioral despair. PharmacolBiochemBehav. 2002; 71:341-344; and Boyer P A, Skolnick P, Fossom L H. Chronic administration of imipramine and cita-lopram alters the expression of NMDA receptor subunit mRNAs in mouse brain: a quantitative in situ hybridization study. J MolNeurosci. 1998; 10:219-233, incorporated by reference herein in their entireties.)

As is known to those of ordinary skill in the art, ketamine is a drug used in human and veterinary medicine, primarily for the induction and maintenance of general anesthesia, usually in combination with a sedative. Other uses include sedation in intensive care, analgesia (particularly in emergency medicine), and treatment of bronchospasm. Ketamine has a wide range of effects in humans, including analgesia, anesthesia, hallucinations, elevated blood pressure, and bronchodilation.

Pharmacologically, ketamine is classified as an NMDA receptor antagonist. At high, fully anesthetic level doses, ketamine has also been found to bind to μ-opioid receptors type 2 in cultured human neuroblastoma cells—however, without agonist activity—and to sigma receptors in rats.

Also, ketamine interacts with muscarinic receptors, descending monoaminergic pain pathways and voltage-gated calcium channels.

Several lines of evidence from studies also suggest that dysfunction of the glutamatergic system may play an important role in the pathophysiology of depression. As is known to those skilled in the art, glutamic acid is one of the 20-22 proteinogenic amino acids, and the carboxylate anions and salts of glutamic acid are known as glutamates. In neuroscience, glutamate is an important neurotransmitter. The NMDA receptor is a glutamate receptor. Nerve impulses trigger release of glutamate from the pre-synaptic cell. In the opposing post-synaptic cell, glutamate receptors, such as the NMDA receptor, bind glutamate and are activated. In clinical trials, the glutamatergic modulators lamotrigine and riluzole (both inhibitors of glutamate release) were found to have antidepressant properties. Further, a recent study by Sanacora et al showed glutamate levels in the occipital cortex to be significantly elevated in 29 medication-free subjects with unipolar major depression as compared with 28 age- and sex-matched healthy controls (Sanacora G, Gueorguieva R et al., Subtype-specific alterations of gamma-am inobutyric acid and glutamate in patients with major depression., Arch Gen Psychiatry. 2004; 61:705-713, incorporated by reference herein in its entirety). Together, these data support the hypothesis of regional alterations in glutamatergic signaling in mood disorders.

Based on the preclinical and preliminary clinical studies, NMDA receptor complex may mediate the delayed therapeutic effects of traditional monoaminergic-based antidepressants and, furthermore, that directly targeting the NMDA receptor could bring about rapid antidepressant effects. Indeed, first in a preliminary study of 8 subjects with major depression, it was reported that a single dose of the noncompetitive NMDA receptor antagonist ketamine resulted in a rapid and short-lived antidepressant effect. (See Berman R M, Cappiello A, Anand A, Oren D A, Heninger G R, Charney D S, Krystal J H. Antidepressant effects of ketamine in depressed patients. Biol Psychiatry. 2000; 47:351-354, incorporated by reference herein in its entirety.)

This first trial was followed by a second trial (a double-blind trial) in a relatively refractory population. This second trial confirmed a rapid (110 minutes), and relatively sustained (1 week) antidepressant response to a single dose of the NMDA antagonist ketamine. (See Zarate, C A Jr, Singh J B et al., Randomized Trial of an N-methyl-D-aspartate Antagonist in Treatment-Resistant Major Depression. Arch Gen Psy 2006; 63: 856-864, incorporated by reference herein in its entirety).

However, as noted above, there are many drawbacks to current NMDA receptor antagonists, such as ketamine. However, the present inventors have discovered that a compound such as d-methadone may not suffer from these drawbacks. As observed by Manfredi (one of the present inventors), patients with severe cancer pain unrelieved by high doses of opioids were achieving relief with very low doses of methadone, less than one twentieth of the expected equianalgesic opioid dose (Manfredi P L, Borsook D, Chandler S W, Payne R. Intravenous methadone for cancer pain unrelieved by morphine and hydromorphone. Pain 1997; 70: 99-101, incorporated by reference herein in its entirety). The NMDA antagonistic activity of d-methadone directly affects pain pathways, as shown by Inturrisi (one of the present inventors) [See Gorman, A. L., Elliott, K. J. and Inturrisi, C. E., The d- and l-isomers of methadone bind to the non-competitive sit on the N-methyl-D-aspartate (NMDA) receptor in rat forebrain and spinal cord, NerurosciLett, 223 (1997) 5-8, incorporated by reference herein in its entirety], but as shown by the inventors in the phase I study described below, d-methadone may also have an effect on pain by directly affecting psychiatric symptoms. Manfredi also observed that patients with history of opioid abuse responded better to methadone compared to other opioids (Manfredi P L, Gonzales G R, Cheville A L, Kornick C and Payne R. Methadone analgesia in cancer pain patients on chronic methadone maintenance therapy. J Pain Sympt Manag. February 2001; 21(2):169-174, incorporated by reference herein in its entirety). This may be due to improvement in analgesia but also improvement of the psychiatric symptoms that often affect these patients and influence the perception of pain intensity. Furthermore, the severe pain escalation noted by Manfredi in patients when methadone was substituted by other opioids may be due to untreated anxiety from sudden lack of NMDA block (Moryl N, Santiago-Palma J, MD, Kornick C, Derby S, Fischberg D, Payne R and Manfredi P. Pitfalls of opioid rotation: substituting another opioid for methadone in the treatment of cancer pain. Pain 2002; 96 (3): 325-328, incorporated by reference herein in its entirety).

In addition, d-methadone has been shown to be safe in clinical studies dating back to the 1950s, and when used together with its isomer as racemic methadone. This safety was shown at doses much higher than those expected to be effective for pain. Furthermore, d-methadone is not addictive and was not recognized as an opioid by heroin addicts and did not work as a substitute for opioids in this patient population. However, the fact that racemic methadone is successfully used for the treatment of addiction may be in part due to the activity of d-methadone at the NMDA receptor. In other words, d-methadone does not work as an opioid substitute the way racemic methadone, which is a potent opioid, does, but d-methadone may be effective for the treatment of the psychological symptoms that commonly outlive and persist beyond the acute opioid withdrawal phase. Often patients detoxified from opioids, after the opioid withdrawal syndrome is over, are treated with antidepressant, antianxiety, and mood stabilizing drugs. Based on the phase I-II study findings described below, the clinical observations of the use of methadone from Manfredi cited above [Manfredi P L, Gonzales G R, Cheville A L, Kornick C and Payne R. Methadone analgesia in cancer pain patients on chronic methadone maintenance therapy. J Pain Sympt Manag. February 2001; 21(2):169-174, incorporated by reference herein in its entirety], and the experimental studies from Inturrisi, also cited above (Gorman, A. L., Elliott, K. J. and Inturrisi, C. E., The d- and l-isomers of methadone bind to the non-competitive sit on the N-methyl-D-aspartate (NMDA) receptor in rat forebrain and spinal cord, NerurosciLett, 223 (1997) 5-8, incorporated by reference herein in its entirety), d-methadone may be more effective than conventional psychiatric drugs in treating depression anxiety and other psychiatric symptoms, including the sub-acute and chronic psychiatric symptoms that follow or are concomitant to stressful events such as pain, cancer, opioid treatment and opioid withdrawal.

In the phase I study developed by the present inventors and performed by investigators (Drs. Natalie Moryl, Dana Tarcatu, and Eugenie Obbens) at Memorial Sloan-Kettering Cancer Center, New York, N.Y. (described in greater detail below) in very sick patients with severe cancer pain, d-methadone was not only well tolerated but it was liked by the patients who recognized it as an effective analgesic.

Thus, based on these results, the present inventors have determined that d-methadone is not only safe but would prove itself analgesic (in a phase II study). The most suitable study would likely be in patients with diabetic neuropathy, similarly to what has been done with other non-opioid analgesics. This pathway to approval would likely be conducive to a widespread use in most pain syndromes: clinicians treating patients with cancer pain and neuropathic pain in addition to those treating non-malignant chronic pain are waiting for safe, non-addictive analgesics, to be used either alone or in combination with opioids and other analgesics.

The NMDA receptor antagonists have received much attention from scientists and industry because of their effects on a crucial chronic pain circuit. Unfortunately the designer high affinity drugs such as MK-801 are not safe. The NMDA antagonists on the market have known problems. Ketamine causes hallucinations, dextrometorphan has a very short half life and memantine a very long one which depends heavily on renal excretion. Also the effects of dextrometorphan and memantine may be too weak to produce analgesia.

On the other hand, d-methadone is proven to be safe and, as determined by the present inventors, has the optimal affinity to be effective for analgesia. Its half life and liver metabolism are other advantages.

In addition to NMDA antagonistic activity, d-methadone is a weak inhibitor of NE reuptake. Codd E E, Shank R P, et al. Serotonin and Norepinephrine activity of centrally acting analgesics: Structural determinants and role in antinociception. IPET 1995; 274 (3)1263-1269 (incorporated by reference herein in its entirety). Thus, this may also contribute to alleviate psychiatric symptoms, especially depression.

Additionally, Krystal et al. [Krystal J H, D'Souza D C, Petrakis I L, Belger A, Berman R M, Charney D S, Abi-Saab W, Madonick S., NMDA agonists and antagonists as probes of glutamatergic dysfunction and pharmacotherapies in neuropsychiatric disorders., Hary Rev Psychiatry. 1999 September-October; 7(3):125-43 (incorporated by reference herein in its entirety)] suggest that the degree to which NMDA antagonists produce effects within a given domain is related to the extent of the environmental stimulation within that domain. This particular mode of action may be important when the NMDA receptors of patients are abnormally stimulated as may happen with depression, stress provoking situations and anxiety disorders, including those occurring with substance withdrawal.

EXAMPLE

The following describes the phase I study (referenced above) of d-methadone administered to patients with chronic pain. In particular, investigators at Memorial Sloan-Kettering Cancer Center (of New York, N.Y.) performed a study of d-methadone administered to patients with chronic pain at a dose of 40 mg every 12 hours for 12 days. The following details the results of the phase I portion of that study.

Protocol Summary

The study was a Phase I open label study of d-methadone in patients with chronic pain and multiple co-morbidities. Seven out of eight patients completing the study had advanced cancer. The patients were taking an average of 5 different drugs. And all patients had persistent pain despite strong opioids and other analgesics titrated to effect. The objective of the study was to determine if 40 mg of d-methadone administered every 12 hours to chronically ill patients with chronic pain is safe and well tolerated.

The background and rationale for the study was as follows: (1) Tolerance to opioid analgesia necessitates dose escalation, which can result in an increase in adverse effects; (2) NMDA receptor antagonists attenuate chronic pain, especially neuropathic pain; and (3) NMDA receptor antagonists attenuate and reverse opioid analgesic tolerance [Inturrisi, C. E. "Opioid Analgesic Therapy in Cancer Pain," Advances in Pain Research and Therapy, (K. M. Foley, J. J. Bonica, and V. Ventafridda, Eds.) pp. 133-154, incorporated by reference herein in its entirety].

Both d-methadone and l-methadone are NMDA antagonists. Only l-methadone binds to opioid receptors. Treatment with d-methadone results in NMDA antagonism without opioid receptor activity. [See Gorman, A. L., Elliott, K. J. and Inturrisi, C. E., The d- and l-isomers of methadone bind to the non-competitive sit on the N-methyl-D-aspartate (NMDA) receptor in rat forebrain and spinal cord, Nerurosci Lett, 223 (1997) 5-8, incorporated by reference herein in its entirety.]

Thus, d-methadone could be used as an independent non-opioid analgesic for patients with chronic pain. Further, d-methadone could be added to opioids to prevent tolerance and dose escalation.

Criteria for Patient Eligibility

In order to be considered eligible for the study, individuals had to: (1) be experiencing chronic pain, and had to have experienced pain greater than or equal to 3 on a 0-10 visual analogue scale (VAS) in the previous 24 hours; (2) be 18 years of age or older; (3) have a KPS (Karnofsky Performance Status) of greater than or equal to 80; (4) not be pregnant; and (5) have a responsible companion living with them during the study (12 days).

Any of the following would serve to exclude an individual from the study: (1) a known hypersensitivity to methadone; (2) if the patient was taking methadone or previous methadone treatment within one month of enrollment (3) any changes in the dose of the following medications within 2 weeks of study enrollment: Abacavir, Benzodiazepines, Carbamazepine, Efavirnez, Fluconazole, Fluvoxamine, Neltrexone, Nelfinavir, Nevirapine, Phenytoin, Risperidone, Ritonavir, AZT, St. John's Wort; or (4) a baseline QTc>0.440/year.

Once individuals were selected, they were given a pre-treatment examination, to diagnose and determine: (1) pain diagnosis, (2) analgesic regimen and concurrent pharmacological therapies, (3) existing side effects, (4) the Symptom Assessment Sheet-BaselineEKG, (5) mini-mental state examination (MMSE), and (6) renal and liver function tests.

305 individuals were screened for participation in the study. 295 patients were excluded for not meeting the inclusion criteria, or other reasons (e.g., did not choose to participate). 10 patients signed a consent to participate in the study. However, one patient became ineligible before the study began, and one patient was removed from the study based on that patient's request. 8 patients completed the study.

Methods

Administration of d-methadone was at 40 mg PO q12 hr for 12 days. Patients visited the clinic on days 1, 8, and 12. The patients also kept a daily diary (concerning side effects and analgesia). Doctors involved in the study also kept a daily diary (based on daily phone interviews with the patients). Serum d-methadone level for each patient was measured 6 hours after the morning dose on day 12. EKGs of each patient were taken on days 1, 8, and 12. A MMSE was given to each patient on days 1 and 12. And a Global Assessment for pain and Global Assessment for mood was determined for each patient on day 12.

Results

Results are shown in Tables 1-3 (below) and the discussion thereafter.

TABLE 1

Results - Demographics

| Patient # | Race | Gender | Diagnosis | Pain diagnosis |
|---|---|---|---|---|
| 01 | WNH | f | meningioma | back pain due to metastatic disease |
| 56 | WNH | m | renal cell carcinoma | back pain/postthoracotomy pain |
| 117 | WNH | m | lymphoma | back pain due to spinal stenosis, neuropathy |
| 224 | WH | f | lymphoma | neck pain/shoulder pain after lymphoma resection |
| 258 | WNH | m | acute leukemia | hip pain due to avascular necrosis |
|  | BNH | f | breast cancer | chemotherapy induced neuropathy |
|  | WNH | m | degenerative joint disease | degenerative joint disease |
|  | WNH | f | thyroid cancer | arthralgia/neuropathy after chemotherapy |
|  | WNH | f | breast cancer | postmastectomy pain, carpal tunnel syndrome |
| 305 | WH | f | cystadenocarcinoma | chest pain due to chest wall metastases |

TABLE 2

Results - Edmonton Symptom Assessment Scale Administered on day 1 (baseline) and day 12

| Patient | Pain | | Tiredness | | Anxiety | | Well-being (10-the worst) | | Drowsiness | |
|---|---|---|---|---|---|---|---|---|---|---|
|  | Baseline | Day 12 | Baseline | Day 12 | Baseline | Day 12 | Baseline | Day 12 | Baseline | Day 12 |
| 1 | 4 | 5 | 4 | 5 | 4 | 3 | 2 | 0 | 5 | 0 |
| 56 | 7 | 2 | 9 | 4 | 1 | 4 | 0 | 1 | 0 | 2 |
| 117 | 5 | 5 | 8 | 7 | 0 | 0 | 0 | 0 | 0 | 0 |
| 258 | 1 | 5 | 8 | 6 | 0 | 0 | 3 | 3 | 4 | 3 |
| 301 | 3 | 3 | 0 | 0 | 3 | 1 | 0 | 0 | 6 | 1 |
| 302 | 6 | 9 | 5 | 5 | 0 | 0 | 2 | 5 | 2 | 1 |
| 303 | 4 | 4 | 6 | 0 | 5 | 2 | 0 | 0 | 6 | 9 |
| 305 | 3 | 0 | 7 | 2 | 7 | 2 | 0 | 1 | 10 | 7 |
|  | 4.1 | 4.1 | 5.9 | 3.6 | 2.5 | 1.5 | 0.9 | 1.3 | 4.1 | 2.9 |

TABLE 3

Results - Summary and attribution of adverse events documented in the diaries AE according to CTCAE v3.0 for 8 patients that completed the study and 1 patient who was removed from the study

| CTCAE v3.0 | AE | # of patients | Grade (1-5) | Attribution |
|---|---|---|---|---|
| Neurology | Somnolence | 2 | 2 | 3 |
|  | Tremor | 1 | 1 | 3 |
| Pain | Back | 1 | 1 | 3 |
|  | Headache | 1 | 1 | 3 |
|  | Headache | 1 | 1 | 4 |

Summary of Results

D-methadone at the dose of 40 mg PO Q 12 hours was well tolerated in this group of patients with chronic pain and multiple co morbidities, though further phase I and phase II studies may be needed to confirm its safety and analgesic effects.

Since d-methadone is likely well tolerated at doses that provide clinically useful NMDA receptor antagonism, it is likely to be useful for the treatment of a wide spectrum of painful conditions.

Upon thorough review of the data from this study the inventors discovered that patients taking d-methadone experienced: (1) Improved well-being: baseline 4.1—after treatment 2.9 (lower numbers indicate improved mood): (2) Less anxiety: baseline 2.5—after treatment 1.5: and (3) Less tiredness: baseline 5.9—after treatment 3.6.

The above numbers indicate average scores for eight patients on Visual Analogue Scales part of the Edmonton Symptom Assessment Score at baseline and on day 12 of treatment with d-methadone 40 mg every 12 hours.

These data signal possible therapeutic benefits from d-methadone for the relief of various psychological symptoms. These findings are enhanced by excluding patients with baseline symptom scores insufficient to be susceptible to clinically relevant improvement. These findings did not correlate to changes in pain scores and, therefore, the present inventors have determined that this suggests clinical indications independent from analgesia.

These new findings, together with the experimental work performed by present inventor Charles Inturrisi [described in Gorman, A. L. et. al, "The d- and l-isomers of methadone bind to the non-competitive site on the N-methyl-D-aspartate (NMDA) receptor in rat forebrain and spinal cord," Neuroscience Letters, 223 (1997) pp. 5-8; Shimoyama, N. et. al, "d-methadone Is Antinociceptive in the Rat Formalin Test," J Pharma and Exper Therap, 293 (1997) pp. 648-652; Davis, A. M. and Inturrisi, C. E., "d-methadone Blocks Morphine Tolerance and N-Methyl-D-Aspartate-Induced Hyperalgesia," J Pharma and Exper Therap, 289 (1999) pp. 1048-1053; and Inturrisi, C. E., "Pharmacology of methadone and its isomers," Minerva Anestesiol 71 (2005), pp. 435-437, incorporated by reference herein in their entireties) and other literature cited in this application suggest a previously unrecognized benefit from d-methadone in many psychiatric syndromes and symptoms. Further, the fact that d-methadone would be beneficial in the treatment of psychiatric symptoms and conditions suggests that similar drugs, such as d-methadol, d-alpha-acetylmethadol, l-alpha-acetylmethadol, d-alpha-normethadol, l-alpha-normethadol, and their pharmaceutically acceptable salts, would also be beneficial in such treatment.

While the various aspects of the present invention have been disclosed by reference to the details of various embodiments of the invention, it is to be understood that the disclosure is intended as an illustrative rather than in a limiting sense, as it is contemplated that modifications will readily occur to those skilled in the art, within the spirit of the invention and the scope of the appended claims.

What is claimed is:

1. A method of treating psychological and psychiatric symptoms, the method of treating consisting of:
   (a) administering a composition to a subject suffering from one or more psychological symptoms chosen from depression, anxiety, fatigue, and mood instability including pseudo-bulbar affect, the composition including, as the sole active agent within the composition, an NMDA receptor antagonist selected from d-methadone, d-methadol, d-alpha-acetylmethadol, d-alpha-normethadol, l-alpha-normethadol, and pharmaceutically acceptable salts thereof; and
   (b) administering a psychiatric drug to the subject, wherein the psychiatric drug is selected from CNS stimulants, opioids, nicotine, and other NMDA receptor antagonists;
   wherein the NMDA receptor antagonist is isolated from its enantiomer or synthesized de novo; and
   wherein the administering of the composition occurs under conditions effective for the NMDA receptor antagonist to bind to an NMDA receptor of the subject and thereby relieve the subject from said one or more psychological symptoms.

2. The method according to claim 1, wherein the NMDA receptor antagonist is d-methadone.

3. The method according to claim 2, wherein the NMDA receptor is capable of biological action, and wherein the administering is effective to block the biological action of the NMDA receptor.

4. The method according to claim 2, wherein the subject has a central nervous system, and wherein the NMDA receptor is located in the central nervous system.

5. The method according to claim 4, wherein the subject is a mammal.

6. The method according to claim 5, wherein the mammal is a human.

7. The method according to claim 1, wherein the administering of the psychiatric drug and the composition is performed orally, nasally, rectally, trans-dermally, parenterally, or topically.

8. The method according to claim 2, wherein the d-methadone in the form of a pharmaceutically acceptable salt.

9. The method according to claim 2, wherein the d-methadone is administered intravenously.

10. The method according to claim 2, wherein the d-methadone is delivered at a total daily dosage of about 1 mg to about 5,000 mg.

11. A method of treating psychological and psychiatric symptoms the method of treating consisting of:
   (a) administering a composition to a subject suffering from one or more psychological symptoms chosen from depression, anxiety, fatigue, and mood instability including pseudo-bulbar affect, the composition including, as the sole active agent within the composition, an NE reuptake inhibitor selected from d-methadone, d-methadol, d-alpha-acetylmethadol, d-alpha-normethadol, l-alpha-normethadol, and pharmaceutically acceptable salts thereof; and
   (b) administering a psychiatric drug to the subject, wherein the psychiatric drug is selected from CNS stimulants, opioids, nicotine, and other NE reuptake inhibitors;
   wherein the NE reuptake inhibitor is isolated from its enantiomer or synthesized de novo; and
   wherein the administering of the composition occurs under conditions effective for the NE reuptake inhibitor to bind to an NE receptor of the subject and thereby relieve the subject from said one or more psychological symptoms.

12. The method according to claim 11, wherein the NE reuptake inhibitor is d-methadone.

13. The method according to claim 12, wherein the NE receptor is capable of biological action, and wherein the administering is effective to inhibit NE reuptake at the NE receptor.

14. The method according to claim 12, wherein the subject has a central nervous system, and wherein the NE receptor is located in the central nervous system.

15. The method according to claim 14, wherein the subject is a mammal.

16. The method according to claim 15, wherein the mammal is a human.

17. The method according to claim 11, wherein the administering of the psychiatric drug and the composition is performed orally, nasally, rectally, trans-dermally, parenterally, or topically.

18. The method according to claim 12, wherein the d-methadone in the form of a pharmaceutically acceptable salt.

19. The method according to claim 12, wherein the d-methadone is administered intravenously.

20. The method according to claim 12, wherein the d-methadone is delivered at a total daily dosage of about 1 mg to about 5,000 mg.

* * * * *

UNITED STATES PATENT AND TRADEMARK OFFICE
CERTIFICATE OF CORRECTION

PATENT NO.       : 9,855,226 B2
APPLICATION NO.  : 15/204052
DATED            : January 2, 2018
INVENTOR(S)      : Paolo L. Manfredi et al.

It is certified that error appears in the above-identified patent and that said Letters Patent is hereby corrected as shown below:

On the Title Page

Column 2, Item [56],
Line 9, "I-isomers" should read -- l-isomers --.

In the Specification

Column 3,
Line 33, "about of the" should read -- about the --.
Line 37, "sit" should read -- site --.

Column 9,
Line 63, "sit" should read -- site --.

Column 10,
Line 46, "sit" should read -- site --.
Line 49, "depression anxiety" should read -- depression, anxiety --.

Column 12,
Line 8, "sit" should read -- site --.

Column 13,
Table 2, the "Drowsiness" column should be the fourth column — not the fifth column, and the "Drowsiness" column should be in alignment with the "Pain", "Tiredness", "Anxiety", and "Well-being (10-the worst)" columns.
Table 2, the "Well-being (10-the worst)" column should be the fifth and final column — not the fourth column.

Column 14,
Line 53, "entireties)" should read -- entireties)] --.

Signed and Sealed this
Nineteenth Day of June, 2018

Andrei Iancu
*Director of the United States Patent and Trademark Office*

CERTIFICATE OF CORRECTION (continued)
U.S. Pat. No. 9,855,226 B2

In the Claims

Column 15,
Line 44, Claim 8, "in the form of" should read -- is in the form of --.
Line 51, Claim 11, "symptoms" should read -- symptoms, --.

Column 16,
Line 43, Claim 18, "in the form of" should read -- is in the form of --.